United States Patent [19]

Bank

[11] Patent Number: 5,126,471
[45] Date of Patent: Jun. 30, 1992

[54] THERMAL DISPROPORTIONATION OF CYCLOALKYLSILANES

[75] Inventor: Howard M. Bank, Freeland, Mich.

[73] Assignee: Dow Corning Corporation, Midland, Mich.

[21] Appl. No.: 791,696

[22] Filed: Nov. 14, 1991

[51] Int. Cl.$^5$ ................................................. C07F 7/08
[52] U.S. Cl. .................................................... 556/469
[58] Field of Search ......................................... 556/469

[56] References Cited

U.S. PATENT DOCUMENTS

| | | | |
|---|---|---|---|
| 2,223,983 | 11/1955 | Bailey | 556/469 |
| 2,530,367 | 11/1950 | Hance et al. | 556/469 X |
| 2,746,981 | 5/1956 | Wagner | 556/469 |
| 4,667,047 | 5/1987 | Imaki et al. | 556/469 |

FOREIGN PATENT DOCUMENTS 62-263189  11/1987  Japan .

OTHER PUBLICATIONS

Gilman et al., J. Org. Chem. 23:326–328 (1958).
Eaborn et al., J. Organometal. Chem. 4:489 (1965).

*Primary Examiner*—Paul F. Shaver
*Attorney, Agent, or Firm*—William F. Boley

[57] ABSTRACT

The present invention is a process for the thermal disproportionation of cycloalkylsilanes containing at least one hydrogen atom and one halogen atom bonded to a single silicon atom. The process involves heating the cycloalkylsilanes in a liquid phase to a temperature within a range of about 250° C. to 450° C. The present process is especially useful for the thermal disproportionation of cyclopentyldichlorosilane to dicyclopentyldichlorosilane and for the thermal disproportionation of cyclohexyldichlorosilane to dicyclohexyldichlorosilane.

11 Claims, No Drawings

THERMAL DISPROPORTIONATION OF CYCLOALKYLSILANES

BACKGROUND

The present invention is a process for the thermal disproportionation of cycloalkylsilanes containing at least one hydrogen atom and one halogen atom bonded to a single silicon atom. The process involves heating the cycloalkylsilanes in a liquid phase to a temperature within a range of about 250° C. to 450° C.

It is known that disproportionation of monoaryldichlorosilanes occurs in the presence of Friedel-Crafts type catalysts. For example, Wagner. U.S. Pat. No. 2,746,981. issued May 22, 1956. describes a process for the disproportionation of an aryldichlorosilane containing one aryl group and one hydrogen group, by heating the aryldichlorosilane to a temperature of at least 50° C. and a pressure not to exceed atmospheric in the presence of a Friedel-Crafts type catalyst taken from the class consisting of aluminum chloride and boron chloride, and recovering a diarydichlorosilane.

Japanese Patent 62263189, Published Nov. 16, 1987, describes the use of Lewis acid compounds for the disproportionation of aryldihalosilanes under reduced pressure. The catalysts used are described as Lewis acid compounds such as metal halides and aryl metal compounds. Examples of catalysts described in the Japanese patent are aluminum chloride, aluminum bromide, triphenylborane, and tolylborane.

In general, these processes involving the use of a catalyst require that the catalyst either be removed or neutralized prior to distillation to separate the desired product. If the catalyst is not removed, the desired product can be disproportionated during the distillation process, reducing process yield. In addition, catalysts such as AlCl$_3$ easily sublime coating the processing equipment. Therefore, it is an objective of the present invention to provide a disproportionation process that does not present these problems typically associated with the use of catalysts.

Gilman et al., J. Org. Chem. 23:326-328 (1958). describes the uncatalyzed disproportionation of Ph$_2$SiH$_2$ at 100° C. to 300° C. at atmospheric pressure.

Eaborn et al., J. Organometal. Chem. 4:489 (1965). describes a process where phenyltrimethylsilane and trichlorosilane are reacted at 500° C. in the gas phase to give phenyltrichlorosilane and trimethylsilane.

The cited art does not recognize that the cycloalkylsilanes described for use in the present process can be thermally disproportionated. Therefore, it is an objective of the present invention to provide a process for the thermal disproportionation of cycloalkylsilanes. Another objective is to provide a process that does not require a catalyst, thus avoiding the previously mentioned problems typically associated with the use of catalysts to disproportionate arylhalosilanes.

SUMMARY OF INVENTION

The present invention is a process for the thermal disproportionation of cycloalkylsilanes containing at least one hydrogen atom and one halogen atom bonded to a single silicon atom. The process involves heating the cycloalkylsilanes in a liquid phase to a temperature within a range of about 250° C. to 450° C. The present process is especially useful for the thermal disproportionation of cyclopentyldichlorosilane to dicyclopentyldichlorosilane and for the thermal disproportionation of cyclohexyldichlorosilane to dicyclohexyldichlorosilane.

DESCRIPTION OF INVENTION

The present invention is a process for the thermal disproportionation of cycloalkylsilanes. The process comprises: heating cycloalkylsilanes of formula

  (1)

in liquid phase, at a temperature within a range of about 250° C. to 450° C. for a reaction time within a range of about 0.1 to 18 hours. to effect disproportionation to product cycloalkylsilanes of formula

  (2)

where each R is independently selected from a group consisting of cycloalkyls of four to 20 carbon atoms and substituted cycloalkyls of four to 20 carbon atoms. $R^1$ is selected from a group consisting of alkyls of one to 20 carbon atoms. X is a halogen, a=1 or 2, b=0 or 1, c=1 or 2, a+b+c=2 or 3, d=2 or 3, e=0 or 1, f=0 or 1, and d+e+f=2 or 3.

Cycloalkylsilanes which can be thermally disproportionated by the present process are described by formula (1). The cycloalkylsilane can contain one or two substituents R. Each R is a radical independently selected from a group consisting of cycloalkyls of three to 20 carbon atoms and substituted cycloalkyls of three to 20 carbon atoms. By "substituted cycloalkyls" it is meant that one or more of the carbons forming the cyclic ring is substituted with a substituent selected from a group consisting of an alkyl or haloalkyl of one to 20 carbon atoms, chlorine, and bromine where the halogen substituted on the haloalkyl is selected from a group consisting of bromine, chlorine, iodine, and fluorine. The radical R can be, for example, cyclopentyl, cyclohexyl, cycloheptyl, cyclodecyl, methylcyclohexyl, methylcyclopentyl, chlorocyclohexyl, and chloroethylcyclohexyl. Preferred is when R is selected from a group consisting of cyclopentyl and cyclohexyl.

The cycloalkylsilanes described by formula 1 can contain zero or one substituent $R^1$, where $R^1$ is a radical selected from a group consisting of alkyls of one to 20 carbon atoms. $R^1$ can be, for example, methyl, ethyl, propyl, isopropyl, butyl, tert-butyl, and decyl. Preferred is when $R^1$ is methyl.

The cycloalkylsilanes described by formula 1 can contain one or two halogens, X, where each X is independently selected from a group consisting of bromine, chlorine, iodine, and fluorine. The preferred halogen is chlorine.

The cycloalkylsilanes described by formula 1 must contain at least one hydrogen atom bonded to the silicon atom and can contain a maximum of two hydrogen atoms bonded to the silicon atom. It is preferred that the cycloalkylsilane contain one hydrogen atom bonded to the silicon atom.

Examples of cycloalkylsilanes useful in the present process include: cyclopentyldibromosilane, cyclopentyldichlorosilane, cyclopentylchlorosilane, cyclohexyldichlorosilane, cyclohexylchlorosilane, cyclohexylmethylchlorosilane, (chlorocyclohexyl)dichlorosilane, (methylcyclohexyl)dichlorosilane, (chloroethylcyclohexyl)dichlorosilane, and cyclodecyldichlorosilane.

The cycloalkylsilanes are heated in the liquid phase at a temperature within a range of about 250° C. to 450° C.

A preferred temperature for the process is within a range of about 300° C. to 400° C.

The present process can be run in any standard pressure reactor capable of maintaining sufficient pressure to keep the cycloalkylsilanes in the liquid phase at process temperatures. A preferred reactor design is a continuous flow high-pressure coil.

The time required for the disproportionation of the cycloalkylsilanes to occur depends on the temperature at which the process is conducted. In general, reaction times within a range of about 0.1 hour to 18 hours are useful. Preferred is a reaction time within a range of about 0.5 hour to ten hours.

Product cycloalkylsilanes, which can be formed by the present process, are represented by formula 2, where R, $R^1$, and X are as previously described. In the described process, two cycloalkylsilane molecules disproportionate effecting an exchange of an R substituent of one cycloalkylsilane molecule for a hydrogen atom on the silicon atom of the other cycloalkylsilane. Those skilled in the art will recognize that as a result of this disproportionation reaction, a cycloalkylsilane molecule containing an additional R substituent and a second silane containing an additional hydrogen atom will be formed.

The inventor believes that this disproportionation is an equilibrium reaction, where an equilibrium is formed between the cycloalkylsilanes and the product cycloalkylsilanes. Therefore, it may be desirable to separate the equilibrium mixture, by a process such as distillation, and recycle the recovered cycloalkylsilanes back to the present process.

Examples of product cycloalkylsilanes which can be formed by the present process include: dicyclopentyldibromosilane, dicyclopentyldichlorosilane, tricyclopentylchlorosilane, dicyclohexyldichlorosilane, tricyclohexylchlorosilane, dicyclohexylmethylchlorosilane, di(chlorocyclohexyl)dichlorosilane, di(methycyclohexyl)dichlorosilane, di(chloroethylcyclohexyl)dichlorosilane, and cyclodecyldichlorosilane.

To aid in understanding of the present invention, the following examples are provided. The examples are provided for illustration only and are not intended to limit the present claims.

EXAMPLE 1

The thermal disproportionation of cyclopentyldichlorosilane, $(C_5H_9)HSiCl_2$, at 350° C. was evaluated. The evaluation was conducted in a sealed, 8 mm by 25 cm, Pyrex Brand tube. Prior to sealing and use, the Pyrex tube was dried at 120° C. for two hours. A 1.0 ml aliquot of cyclopentyldichlorosilane was added to the dried Pyrex Brand tube and the tube sealed. The tube was then heated in a tube heater, maintained at 350° C., for two hours. At the end of the two hours, the tube was placed in dry ice to cool.

The content of the tube was evaluated using gas liquid chromatography (GLC) with a flame ionization detector (FID). The results are presented in Table 1 as the area percent under the GLC-FID trace, for each of the described compounds.

TABLE 1

| Thermal Disproportionation of $(C_5H_9)HSiCl_2$ at 350° C. | |
|---|---|
| Compound | GLC-FID Area % |
| $(C_5H_9)HSiCl_2$ | 22.6 |
| $(C_5H_9)SiCl_3$ | 48.0 |
| $(C_5H_9)_2SiCl_2$ | 5.3 |

TABLE 1-continued

| Thermal Disproportionation of $(C_5H_9)HSiCl_2$ at 350° C. | |
|---|---|
| Compound | GLC-FID Area % |
| $C_4H_{10}$ | 8.6 |

EXAMPLE 2

The thermal disproportionation of cyclohexyldichlorosilane, $(C_6H_{11})HSiCl_2$, at 350° C. was evaluated. The evaluation process was the same as that described for Example 1, except the heating of the cyclohexyldichlorosilane was conducted for two hours. After the test sample was cooled, it was analyzed by GLC-FID as previously described. The results are presented in Table 2.

TABLE 2

| Thermal Disproportionation of $(C_6H_{11})HSiCl_2$ at 350° C. | |
|---|---|
| Compound | GLC-FID Area % |
| $(C_6H_{11})H_2SiCl$ | 2.3 |
| $(C_6H_{11})HSiCl_2$ | 81.6 |
| $(C_6H_{11})SiCl_3$ | 0.9 |
| $(C_6H_{11})_2SiCl_2$ | 9.7 |

What is claimed is:

1. A process for the thermal disproportionation of cycloalkylsilanes, the process comprising: heating cycloalkylsilanes of formula $$R_aR^1{}_bH_cSiX_{4-a-b-c}$$

in liquid phase, at a temperature within a range 250° C. to 450° C., for a reaction time within a range of 0.1 to 18 hours, to effect disproportionation to product cycloalkylsilanes of formula $$R_dR^1{}_eH_fSiX_{4-d-e-f}$$

where each R is independently selected from a group consisting of cycloalkyls of four to 20 carbon atoms and substituted cycloalkyls of four to 20 carbon atoms. $R^1$ is selected from a group consisting of alkyls of one to 20 carbon atoms, X is a halogen, a=1 or 2, b=0 or 1, c=1 or 2, a+b+c=2 or 3, d=2 or 3, e=0 or 1, f=0 or 1, and d+e+f=2 or 3.

2. A process according to claim 1, where R is selected from a group consisting of cyclopentyl and cyclohexyl.

3. A process according to claim 1, where $R^1$ is methyl.

4. A process according to claim 1, where the halogen is chloride.

5. A process according to claim 1, where the cycloalkylsilanes are selected from the group consisting of cyclopentyldichlorosilane and cyclohexyldichlorosilane.

6. A process according to claim 1, where the temperature is within a range of about 300° C. to 400° C.

7. A process according to claim 1, where the reaction time is within a range of about 0.5 hour to ten hours.

8. A process according to claim 1, where the product cycloalkylsilanes are selected from the group consisting of dicyclopentyldichlorosilane and dicyclohexyldichlorosilane.

9. A process according to claim 1, where the process is conducted in a continuous-flow high-pressure coil type reactor.

10. A process for the thermal disproportionation of cyclopentyldichlorosilane, the process comprising heating cyclopentyldichlorosilane in liquid phase, at a temperature within a range of about 300° C. to 400° C., for a reaction time within a range of about 0.5 hour to ten hours, to effect disproportionation to dicyclopentyldichlorosilane and dichlorosilane.

11. A process for the thermal disproportionation of cyclohexyldichlorosilane, the process comprising heating cyclohexyldichlorosilane in liquid phase, at a temperature within a range of about 300° C. to 400° C., for a reaction time within a range of about 0.5 hour to ten hours, to effect disproportionation to dicyclohexyldichlorosilane and dichlorosilane.

\* \* \* \* \*